United States Patent
Cane' et al.

(10) Patent No.: US 12,042,624 B2
(45) Date of Patent: Jul. 23, 2024

(54) MANUALLY OPERATED MECHANICAL PUMP FOR DRUG INFUSION

(71) Applicant: CANE' S.P.A., Rivoli (IT)

(72) Inventors: Mario Cane', Rivoli (IT); Claudio Cane', Rivoli (IT); Paolo Cane', Rivoli (IT)

(73) Assignee: CANE' S.P.A., Rivoli (IT)

( * ) Notice: Subject to any disclaimer, the term of this patent is extended or adjusted under 35 U.S.C. 154(b) by 519 days.

(21) Appl. No.: 17/400,379

(22) Filed: Aug. 12, 2021

(65) Prior Publication Data
US 2023/0050893 A1 Feb. 16, 2023

(51) Int. Cl.
A61M 5/145 (2006.01)
A61M 5/315 (2006.01)

(52) U.S. Cl.
CPC ...... A61M 5/1452 (2013.01); A61M 5/31586 (2013.01); *A61M 2005/14506* (2013.01)

(58) Field of Classification Search
CPC ...... A61M 2005/3131; A61M 5/31576; A61M 2005/3264; A61M 2205/073; A61M 5/31526; A61M 2005/3115; A61M 2025/0175; A61M 2005/14506; A61M 5/1452; A61M 5/31586
See application file for complete search history.

(56) References Cited

U.S. PATENT DOCUMENTS

| | | | |
|---|---|---|---|
| 2,472,116 | A | 6/1949 | Maynes |
| 6,019,747 | A | 2/2000 | McPhee |
| 6,447,487 | B1 | 9/2002 | Cane' |
| D565,176 | S | 3/2008 | Cane' |
| D659,234 | S | 5/2012 | Cane' |
| 8,172,814 | B2 | 5/2012 | Cane' |
| 9,220,835 | B2 | 12/2015 | Cane' |
| 9,289,549 | B2 | 3/2016 | Cane' |
| 9,463,271 | B2 | 10/2016 | Cane' |
| 10,406,283 | B2 | 9/2019 | Cane' et al. |
| 10,576,199 | B2 | 3/2020 | Sealfon et al. |
| 10,842,930 | B2 | 11/2020 | Cane' |
| 2013/0304021 | A1* | 11/2013 | Cabiri ............ A61M 5/31511 604/506 |
| 2016/0067416 | A1 | 3/2016 | Holtwick et al. |
| 2017/0246396 | A1 | 8/2017 | Wei |
| 2019/0209772 | A1 | 7/2019 | Cane' et al. |
| 2020/0016328 | A1 | 1/2020 | Cane' et al. |
| 2020/0046899 | A1 | 2/2020 | Cane' et al. |

* cited by examiner

Primary Examiner — Brandy S Lee
(74) Attorney, Agent, or Firm — Howson & Howson LLP (57) ABSTRACT

A manually operated mechanical pump for drug infusion through a syringe including a plunger slidable within a syringe body to cause drug contained within the syringe body to exit a front opening of the syringe. The pump has a pump body with an open front end, to which the syringe attaches, and an open rear end, at which a drive member is associated movably relative to the pump body. A pair of thrust members are provided between the drive member and the syringe to impart longitudinal thrust in a distal direction onto the plunger to cause the drug to exit the front opening. An elastic element is provided between the thrust members to store and release elastic energy when the first thrust member proximal to the drive member is manually actuated, thus causing the second thrust member proximal to the syringe to advance as the drug exits the front opening.

11 Claims, 8 Drawing Sheets

MANUALLY OPERATED MECHANICAL PUMP FOR DRUG INFUSION

BACKGROUND

The present invention relates to a manually operated mechanical pump for drug infusion. More particularly, the invention pertains to the field of manually operated medical instruments for infusing drugs in liquid form into the body of a living being.

It is known that, in the medical field, syringes are used for infusing drugs in liquid form into the body of a living being. Such syringes usually comprise an elongated hollow cylindrical body open at its opposite ends, a spout or nozzle intended for the entrance and exit of the drug and located at one of the ends of the hollow body, a plunger axially sliding inside the hollow body, and a rod associated with the plunger and arranged to cause sliding back and forth of the plunger inside the hollow body. The rod can therefore both cause drawing of the drug into the syringe, through the front spout or nozzle, and inject the drug through the same front spout or nozzle. The syringes of known type are usually provided with radial tabs at their open rear base where the plunger enters. These tabs, on one hand, improve grip by the user during the steps of drawing and injecting the liquid, and, on the other hand, they can be used for coupling the syringe, without its sliding rod, to an infusion pump having an attachment portion capable of removably receiving a syringe.

Infusion pumps are known medical devices intended for controlled administration of a liquid, usually a drug contained in a syringe or a vial removably associated with the pump.

The use of drug infusion pumps is particularly advantageous for people undergoing therapies requiring infusion, often in a continued and prolonged manner, of substantial amounts of a drug.

In this field, infusion pumps of the automated type, i.e., equipped with a motor or other electrical devices capable of causing advancement of the syringe plunger, and mechanical pumps, i.e., pumps in which advancement of the plunger is imparted by the user, are known. In the first case, the user's intervention onto the pump is usually limited to the step of programming the pump and to the step of controlling advancement of the plunger, whereas in the second case the user's intervention is extended to the step of causing advancement of the plunger.

Obviously, manually operated mechanical pumps are considerably simpler and less expensive than automated ones since they generally do not involve complex mechanical and electronic devices to automate infusion.

In contrast, manually operated mechanical pumps are generally not capable of causing the plunger to move forward accurately following a predetermined infusion or therapy law. Therefore, manually operated mechanical pumps are generally not suitable for use in therapies for which high delivery accuracy in a predetermined time is required.

Recently, however, therapies have become popular that involve infusing drugs in substantial amounts, in relatively short periods of time, and that do not require precisely adhering to predefined delivery curves. The only precaution that is generally necessary to adopt in these therapies is not to exceed a predetermined threshold of amount of drug delivered in the time unit, so as not to cause damage to the patient.

Due to the diffusion of these therapies and of the corresponding drugs on which these therapies are based, today there is a great need for simple and economical manually operated mechanical pumps, which are easy to use for the patient and for the operators and which possibly guarantee a good precision in the drug delivery in the time unit.

Known manually operated mechanical pumps typically comprise a spring element, which is manually loaded in order to later release the accumulated kinetic energy to cause advancement of the syringe plunger.

Document EP3525846 (A1) discloses a pump for drug infusion comprising a body having attachment means for removably attaching a syringe. The pump body is adapted to house a spring arranged for pushing the syringe plunger in order to effect infusion of the drug into the body of a living being.

However, current manually operated mechanical infusion pumps have a number of drawbacks.

First, known pumps do not allow the use of large-sized syringes and, in particular, long syringes, due to the limitation of the spring deformation capacity.

Another drawback stems from the poor ability of manually operated mechanical pumps to accommodate the user's desire to vary the speed of delivery, i.e., the amount of drug in the time unit, for example due to the fact that the spring cannot be compressed again during drug infusion.

A further drawback of known manually operated mechanical pumps stems from their constructive complexity, which results into high production costs and prevents the spread of these pumps in the "poor" sectors, where availability of pumps at low price, reusable several times and whose performance does not vary substantially over time, is required.

A first object of the invention is to provide a manually operated mechanical pump for drug infusion by means of a syringe removably engaged in the pump that does not have the drawbacks of prior art.

A further object of the invention is to provide a manually operated mechanical pump for drug infusion that allows adjustment of the flow of drug to be delivered, thus allowing controlled administration of the drug contained within the syringe.

A still further object of the invention is to provide a manually operated mechanical pump for drug infusion that allows easy loading of the spring, thus allowing even a weak person to carry out this operation.

Not least object of the invention is to provide a manually operated mechanical pump for drug infusion that can be manufactured industrially at low cost.

These and other objects are achieved with a manually operated mechanical pump for drug infusion, as claimed in the appended claims.

SUMMARY

The invention relates to a manually operated mechanical pump capable of delivering the drug contained in a syringe rearwardly attached to the pump in a removable manner. The syringe used for the pump of the invention is essentially a syringe free from the rod and provided with a plunger sliding inside the body of the syringe in order to cause the drug contained in the syringe body to exit through a front opening of the syringe.

The pump according to the invention mainly comprises a pump body having a first, open front end, at which the rear portion of the syringe is attached. The pump body further comprises a second, open rear end, at which a drive member is associated movably relative to the pump body. In a preferred embodiment of the invention, the drive member comprises a knob rotatably associated with the pump body at the second, open rear end. In other embodiments, the drive member may comprise, for example, a rotatable ring nut, a small wheel, a sliding cursor. In other embodiments, a conventional syringe provided with sliding rod or plunger may be used, on condition that space for housing the rod is provided in the pump body.

According to the invention, a pair of thrust members are provided between the drive member and the syringe, the thrust members being adapted to impart a longitudinal thrust in the distal direction onto the plunger of the syringe to cause the drug to exit through the front opening of the syringe. An elastic element is advantageously provided between the thrust members, the elastic element being adapted to store elastic energy when the first thrust member, proximal to the knob, is manually actuated by a user of the pump and some drug to be injected is present within the syringe. Still according to the invention, the elastic element is further adapted to release the stored elastic energy, thus causing the second thrust member proximal to the syringe to advance as the drug exits through the front opening of the syringe. According to the invention, the elastic element is preferably a helical spring, but it may also be a spring of a different kind, or it may comprise an elastic element, for example a compressible dowel, made of rubber or other suitable material.

Preferably, the first thrust member is moveable longitudinally and is guided in its longitudinal movement by a rotatable guide cooperating with the drive member. The first thrust member preferably comprises a rod having an externally threaded portion, and the rotatable guide preferably comprises an internally threaded nut, whereby rotation of the nut causes longitudinal movement of the rod both in the distal direction with respect to the drive member and in the proximal direction, depending on the direction in which the drive member is moved. For example, when the drive member is made as a knob, a clockwise rotation of the knob preferably causes longitudinal advancement of the first thrust member and a counter-clockwise rotation of the knob accordingly causes longitudinal retraction of the first thrust member.

According to a preferred embodiment of the invention, there is provided a friction mechanism adapted to prevent drug infusion when the resistance to advancement of the second thrust member exceeds a predetermined threshold. Such drug infusion might indeed be detrimental to the patient due to a threshold of tolerance of drug amount per time unit being exceeded, which threshold usually depends on the type of drug and the patient's body mass.

Preferably, according to the invention, the friction mechanism is provided between the drive member and the rotatable guide and is adapted to keep the drive member and the rotatable guide in mutual engagement when a force applied to the guide and opposing rotation thereof is below a predetermined threshold.

According to a preferred embodiment of the invention, an indicator showing the relative position between the two thrust members is provided between the two thrust members, the indicator being adapted to visually indicate the load state of the elastic element. The indicator preferably comprises an index and a graduated scale that are moveable relative to each other, the graduated scale indicating a minimum value and a maximum value, and possibly intermediate values, that are visible from the outside of the pump body.

Preferably, according to the invention, the elastic element is chosen so that the difference between the length of the elastic element in its maximum load configuration and the length of the elastic element in its fully relaxed configuration is lower than the distance to be traveled by the plunger of the syringe in order to cause delivery of all of the drug contained within the syringe. In this way, advantageously, it is necessary to perform more than one cycle of compression and relaxation of the elastic element must be carried out in order to completely empty the syringe.

According to the invention, the pump body is preferably obtained by means of a pair of half-shells associated with each other along a longitudinal plane and secured to each other by known means such as screws or an adhesive. The pump body may, for example, be made of plastics, and the same applies to the all the inner members, except for the elastic element, which preferably consists of a metal or elastomeric spring.

In order to attach the syringe to the pump body at the front opening, a pair of diametrically opposite radial grooves are preferably provided, in which radial tabs provided at the base of the syringe are received, this essentially resulting in a bayonet-type fitting for the syringe. In other embodiments of the pump, it will be possible to provide other types of fitting for the syringe, for example for attaching syringes having no tabs and provided with a circumferential groove for engaging locking teeth.

The operation of the pump is as follows.

In a first step of the operation cycle of the pump, also referred to as priming step of the pump, where required, the drive member is actuated to cause retraction of the first thrust member. Retraction of the first thrust member occurs by virtue of the fact that the friction mechanism keeps the drive member in engagement with the rotatable guide. Retraction of the first thrust member causes the two thrust members to move away from each other, with a resulting relaxation of the elastic element. When the first thrust member is completely retracted with respect to the second thrust member, the mutual interference between the two thrust members causes a corresponding simultaneous retraction of both thrust members by acting onto the drive member. At the end of this step, the indicator of the relative position between the two thrust members will be positioned at the minimum value.

In a second step of the operation cycle of the pump, a syringe filled with the drug is attached to the pump body at the front opening by means of the bayonet-type fitting. In this configuration, the syringe plunger is in a retracted position, i.e., proximal to the rear end of the syringe, and the second thrust member is frontally in abutment against the plunger.

In a third step of the operation cycle of the pump, also referred to as loading and infusion step, the drive member is actuated in order to cause advancement of the first thrust member. Advancement of the first thrust member occurs by virtue of the fact that the friction mechanism keeps the drive member in engagement with the rotatable guide. As known, delivery of the drug through the front opening of the syringe occurs with some difficulty, which also depends on the resistance to infusion, exerted by the patient's body and opposing longitudinal advancement of the syringe plunger. Because of this, the longitudinal advancement of the first thrust member caused by the user's actuation of the drive member, initially causes compression of the elastic element arranged between the two thrust members. When the effort required to cause further advancement of the first thrust member is excessive and higher than a predetermined threshold, the friction mechanism prevents further advancement of the first thrust member by means of the actuation of the drive member. At the end of this step, the indicator of the relative position between the two thrust members will be positioned at the maximum value.

During this loading and infusion step, the elastic force of the elastic element, which is loaded because of the mutual approaching of the two thrust members, causes gradual longitudinal movement of the second thrust member, advancement of the plunger, and consequent drug delivery through the front opening of the syringe.

As the elastic element releases its elastic energy stored during the loading step, the effort required to cause advancement of the first thrust member becomes lower than the predetermined threshold and therefore the friction mechanism allows to re-establish the engagement between the drive member and the rotatable guide. Thus, by acting again onto the drive member, it is possible to restore again the load of the elastic element until the predetermined threshold determining friction of the mechanism is reached.

BRIEF DESCRIPTION OF DRAWINGS

Some preferred embodiments of the invention will be described below by way of non-limiting example with reference to the annexed drawings, in which.

DETAILED DESCRIPTION

Referring now to the annexed Figures, there is illustrated a manually operated mechanical pump 11 according to a preferred embodiment of the invention. The pump 11 is capable of delivering the drug contained in a syringe 13 rearwardly attached to the pump 11 in a removable manner.

The syringe 13 is a syringe provided with a plunger 15 sliding inside the syringe body 17 in order to cause exit of the drug contained in the syringe body through a front opening 19 of the syringe. The syringe 13 can be of the type provided with a removable rod associated with the plunger, by means of which rod drawing of the drug into the syringe is caused. In this case, the rod will be removed prior to attaching the syringe to the pump.

The pump 11 comprises a pump body 21 provided with a first open front end 23, at which the rear end 25 of the syringe 13 is attached. The pump body 21 further comprises a second, open rear end 27, at which a drive member 29 is associated movably with respect to the pump body. In the illustrated embodiment, the drive member comprises a corresponding knob 37 rotatably associated with the pump body 21 at the second, open rear end 27.

A pair of thrust members 31, 33 are provided between the drive member 29 and the syringe 13, the thrust members being adapted to impart a longitudinal thrust in the distal direction onto the plunger 15 of the syringe 13 to cause the drug to exit through the front opening 19 of the syringe 13. An elastic element 35 is provided between the thrust members 31, 33, the elastic element being adapted to store elastic energy when the first thrust member 31, proximal to the knob 37, is advanced by a user manually actuating the drive member 29 of the pump 11 and some drug to be injected is present within the syringe 13, and to release the stored elastic energy, thus causing the second thrust member 33, proximal to the syringe 13, to advance as the drug exits through the front opening 19 of the syringe 13.

The first thrust member 31 is moveable longitudinally and is guided in its longitudinal movement by a rotatable guide 39 cooperating with the knob 37. The first thrust member 31 comprises a rod 41 having an externally threaded portion 41a, and the rotatable guide 39 comprises an internally threaded nut 43, whereby rotation of the nut 43 causes longitudinal movement of the rod 41. In the illustrated embodiment, when viewing the knob 37 from below, a rotation of the knob in the clockwise direction causes longitudinal advancement of the first thrust member 31, and a rotation of the knob in the counter-clockwise direction causes longitudinal retraction of the first thrust member 31.

A friction mechanism 45 is provided between the knob 37 and the rotatable guide 39, the friction mechanism being adapted to keep the knob 37 and the nut 43 in mutual engagement, when a force opposing rotation of the nut 43 and being below a predetermined threshold is applied to the nut 43.

Figure 7:
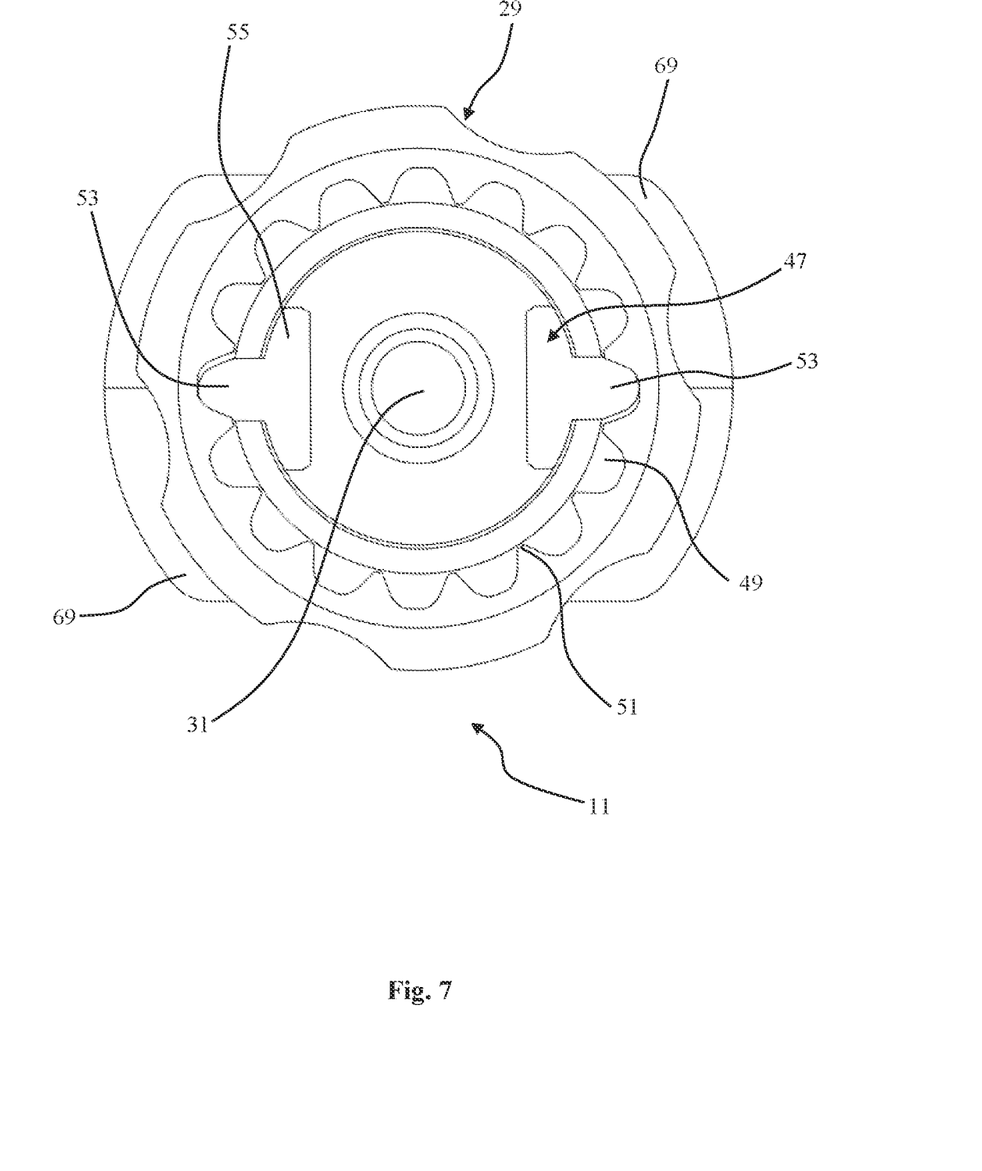
FIG. 7 is a plan view of the friction mechanism.
Figure 8:
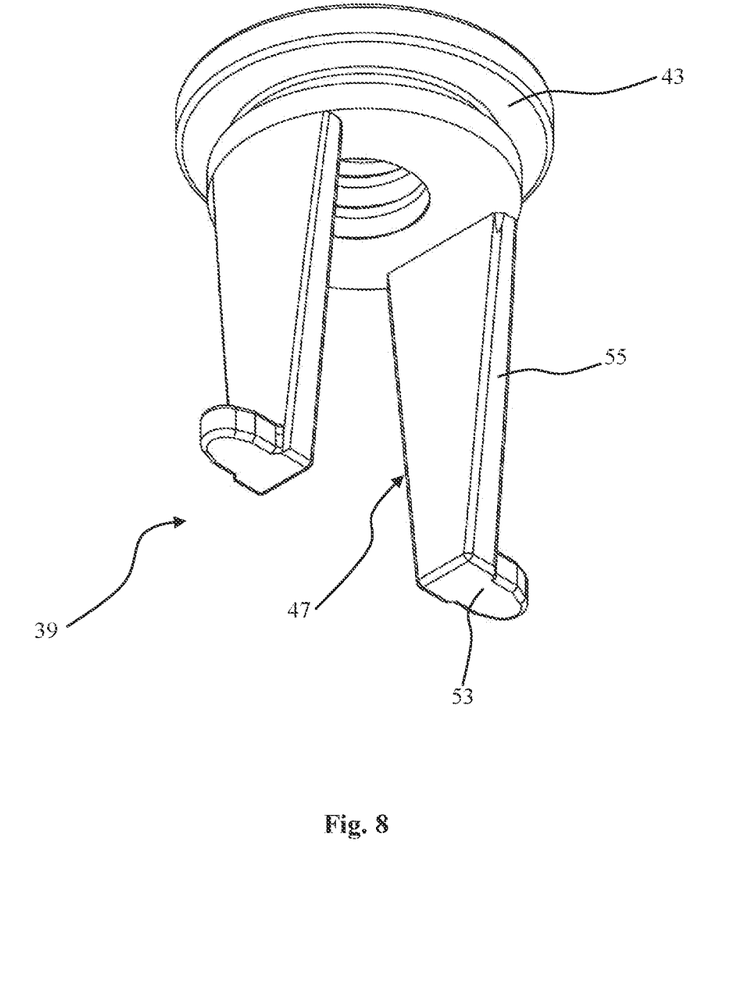
FIG. 8 is a perspective view of the nut and arms of the friction mechanism.

Referring in particular to FIGS. 7 and 8, the friction mechanism 45 comprise a pair of longitudinal arms 47 parallel to the rotation axis of the knob 37 and rotationally integral with the nut 43, the arms extending inside the knob 37 perpendicularly to the plane of rotation of the nut 43. In addition, the friction mechanism 45 comprises a plurality of radial grooves 49 alternated with a corresponding number of radial projections 51, both the grooves and the projections extending longitudinally along the inner wall of the knob 37. The arms 47 comprise each, at the end opposite to the nut 43, a radial appendix 53 adapted to interfere with the radial projections 51 in order to keep the nut 43 in engagement with the knob 37. The arms 47 further comprise a slightly resilient leg 55 capable of allowing radial movement of the appendix 53 when the appendix 53 interferes with the plurality of radial grooves 49 and radial projections 51. The shape of the radial grooves 49, the projections 51 and the radial appendices 53 of the arms 47 is chosen so as to keep the knob 37 in a configuration of engagement with the nut 43, as long as a force opposing rotation of the nut 43 and being lower than a predetermined threshold is exerted onto the nut 43. When the threshold is exceeded, the chosen shape and the elasticity of the legs 55 of the arms 47 allows rotational friction of the radial projections 53 within the grooves 49 and the resulting disengagement of the nut 43 from the knob 37, as long as the force does not become reduced below the predetermined threshold. In this way, excessive drug delivery through the syringe 13 attached to the pump 11 is prevented.

An indicator 57 showing the relative position taken by the two thrust members 31,33 is provided between the two thrust members 31, 33. The indicator is provided with an index 59, which is integral with the first thrust member 31, as well as with a graduated scale 61, which is integral with the second thrust member 33, the index and graduated scale being visible from the outside of the pump body 11.

A longitudinal seat 63 housing the elastic element 35 is defined between the two thrust members 31, 33. The elastic element 35 comprises a coil spring 65 adapted to be loaded longitudinally when the mutual distance between the two thrust members 31, 33 decreases, and to discharge the stored elastic energy to move the two thrust organs 31, 33 away from each other, thereby causing longitudinal sliding of the plunger 15 of the syringe 13 attached to the pump 11. In the illustrated embodiment, the second thrust member 33 comprises a head or pusher 33a capable of interfering with the plunger 15 of the syringe in order to cause advancement thereof. Advantageously, however, according to this embodiment, the interference cannot cause retraction of the plunger 15 of the syringe, when the second thrust member 33 is retracted, because this might cause some depression within the syringe and consequent drawing of the drug from the body of the patient undergoing therapy.

The longitudinal seat 63, provided between the two thrust members 31, 33 further houses a tip 67, the longitudinal extension of which determines the minimum distance between the two thrust members 31, 33 and the maximum load of the spring 65. The tip 67, in this embodiment, is made integral with the second thrust member 33 and interferes with the first thrust member 31 when the thrust members 31, 33 are in their configuration of minimum distance between each other.

The spring 65 is chosen so that the difference between the length of the spring 65 when the spring is in a maximum load configuration and the length of the spring when the spring is in a fully relaxed configuration is lower than the distance to be traveled by the plunger 15 of the syringe 13 in order to cause delivery of all of the drug contained within the syringe 13, whereby it is necessary to perform more than one cycle of compression and relaxation of the spring 65 in order to empty the syringe 13.

The pump body 21 is obtained by means of a pair of half-shells 69 associated with each other along a longitudinal plane and secured to each other by means of screws (not shown) engaged in holes 71 provided in one of the half-shells.

In order to attach the syringe 13 to the pump body 21 at the front opening 23, a pair of diametrically opposite radial grooves 73 are preferably provided, in which radial tabs 75 provided at the base of the syringe 13 are received, this essentially resulting in a bayonet-type fitting for the syringe.

Operation of the pump 11 made according to the described preferred embodiment will now be described in detail.

Figure 1:
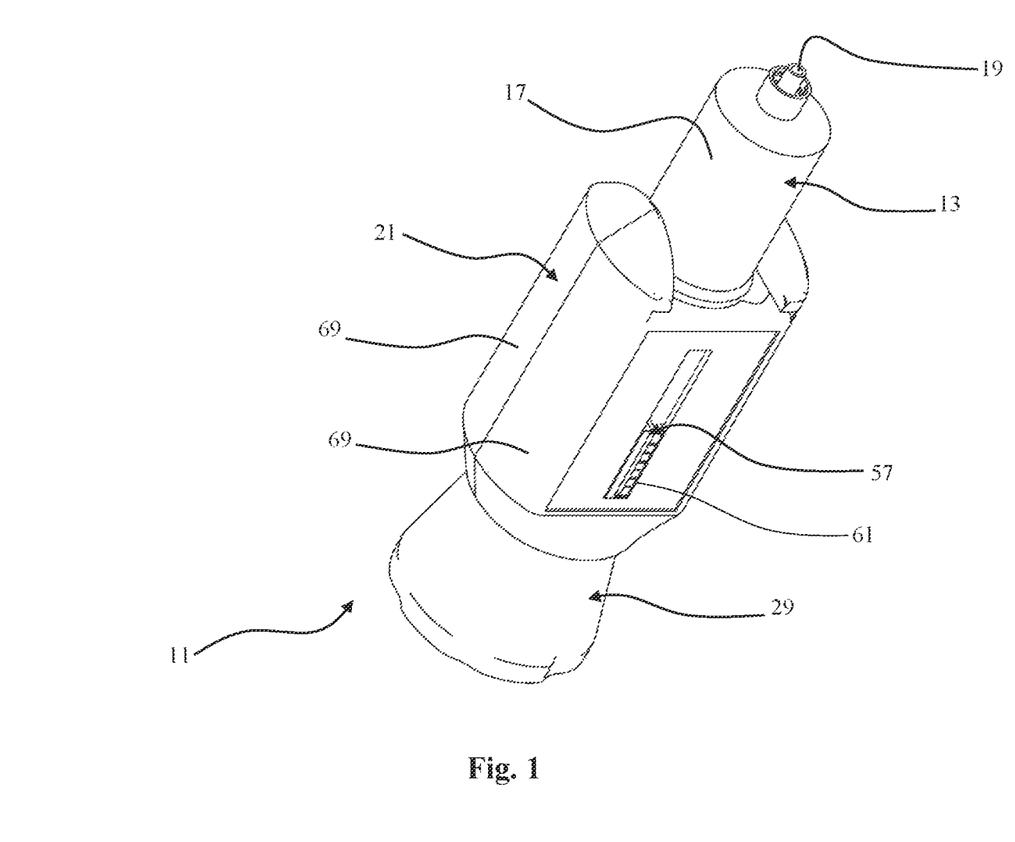
FIG. 1 is a perspective view of a pump according to a preferred embodiment of the invention.
Figure 2:
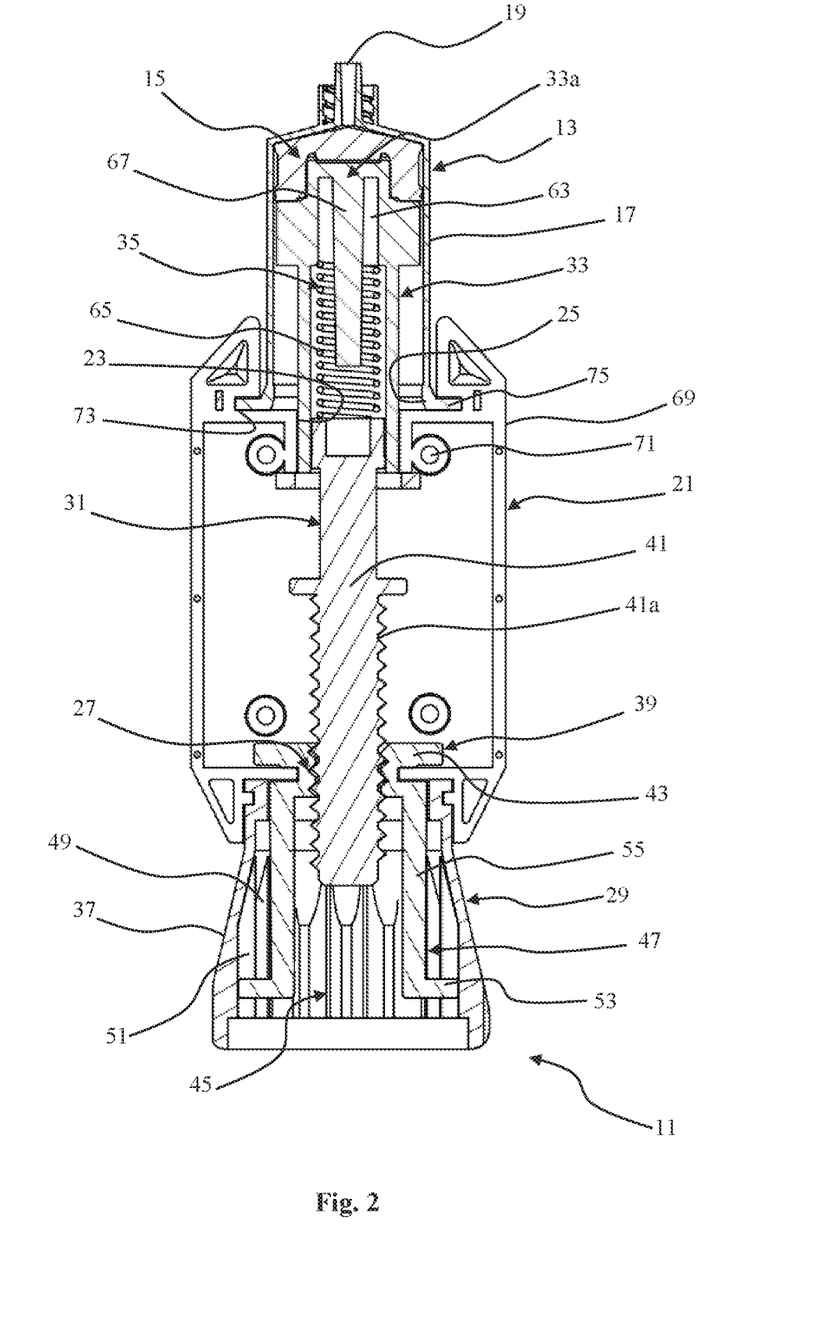
FIG. 2 is a sectional view along a first longitudinal plane of the pump of FIG. 1 when the syringe is empty and the spring is unloaded.
Figure 3:
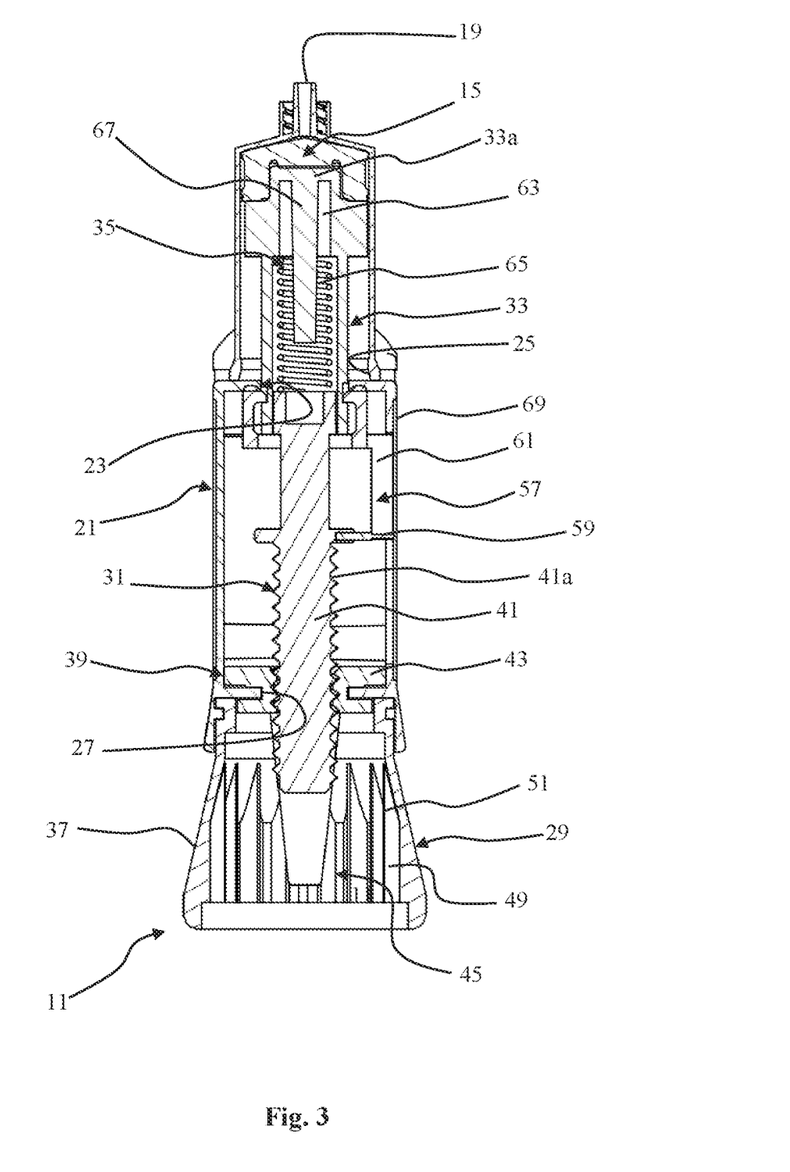
FIG. 3 is a sectional view along a second longitudinal plane rotated by 90° with respect to the sectional plane of FIG. 2 of the pump of FIG. 1 when the syringe is empty and the spring is unloaded.
Figure 4:
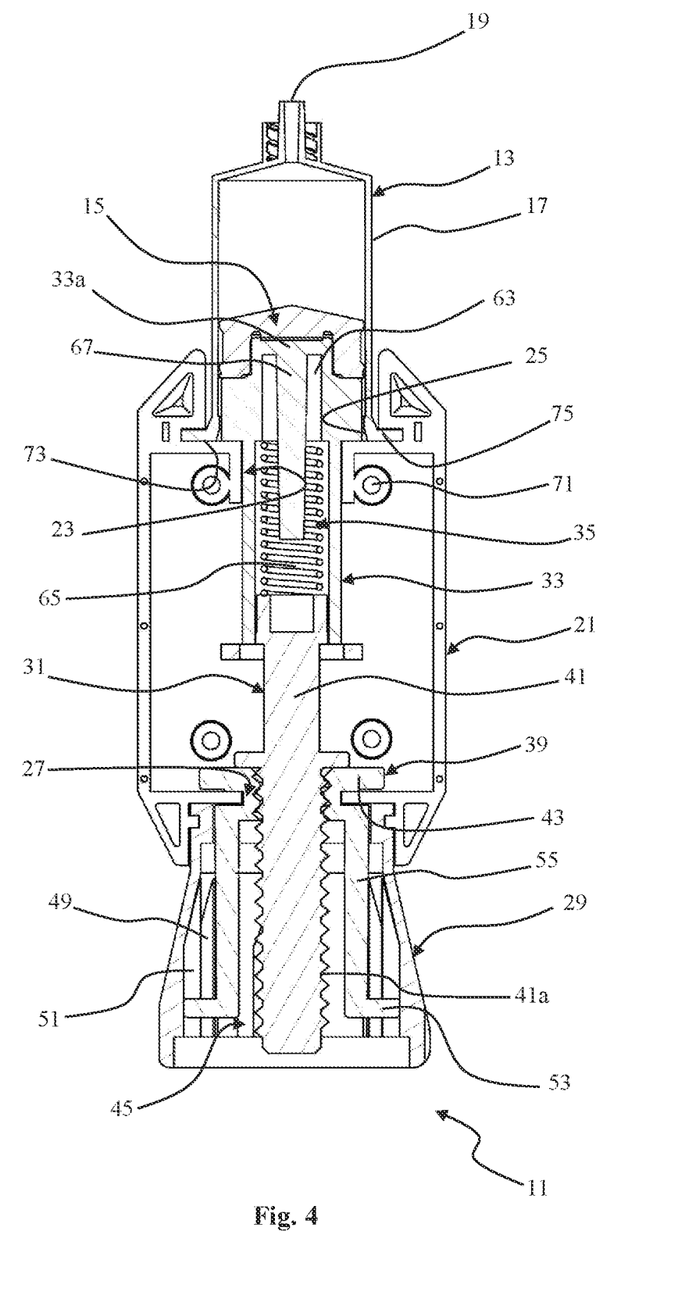
FIG. 4 is a sectional view along the first longitudinal plane of the pump of FIG. 1 when the syringe is full and the spring is unloaded.
Figure 5:
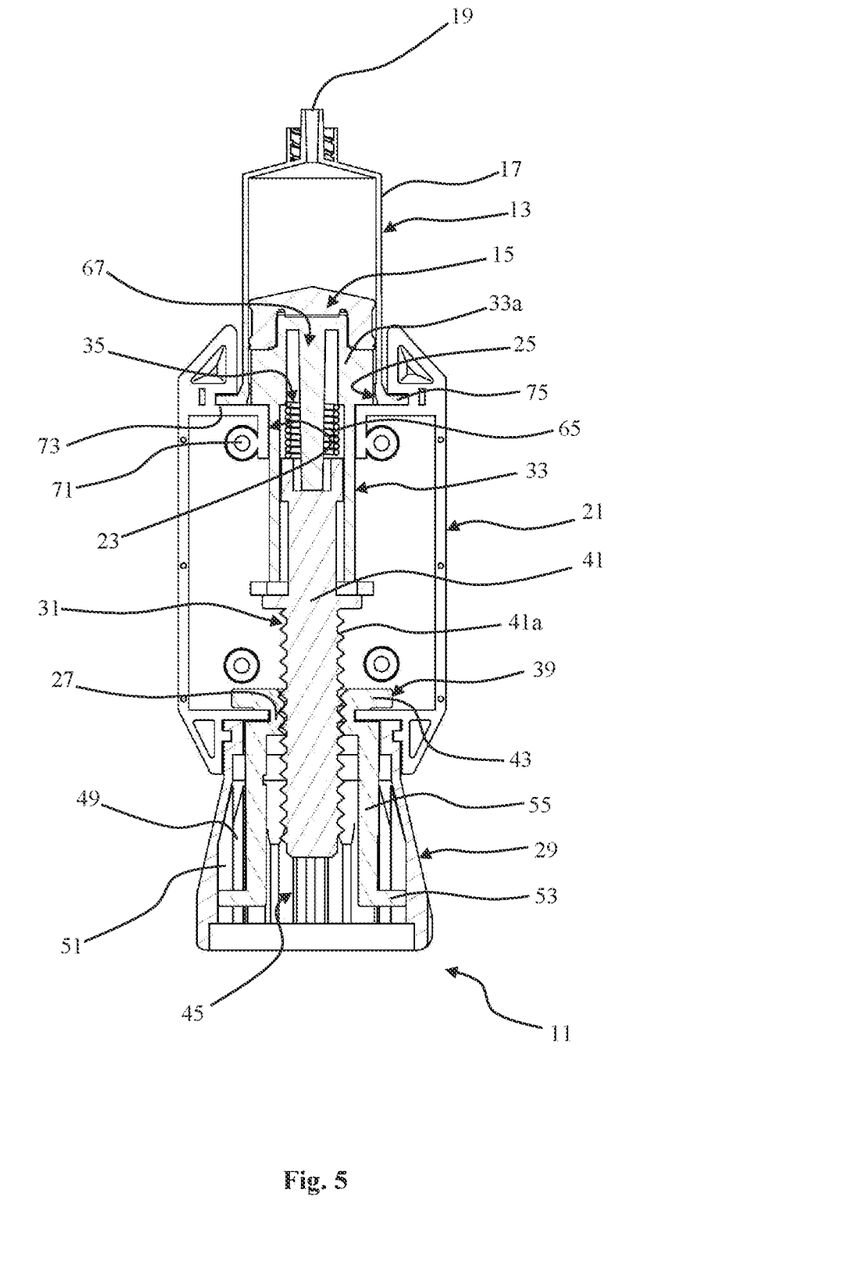
FIG. 5 is a sectional view along the first longitudinal plane of the pump of FIG. 1 when the syringe is full and the spring is loaded.
Figure 6:
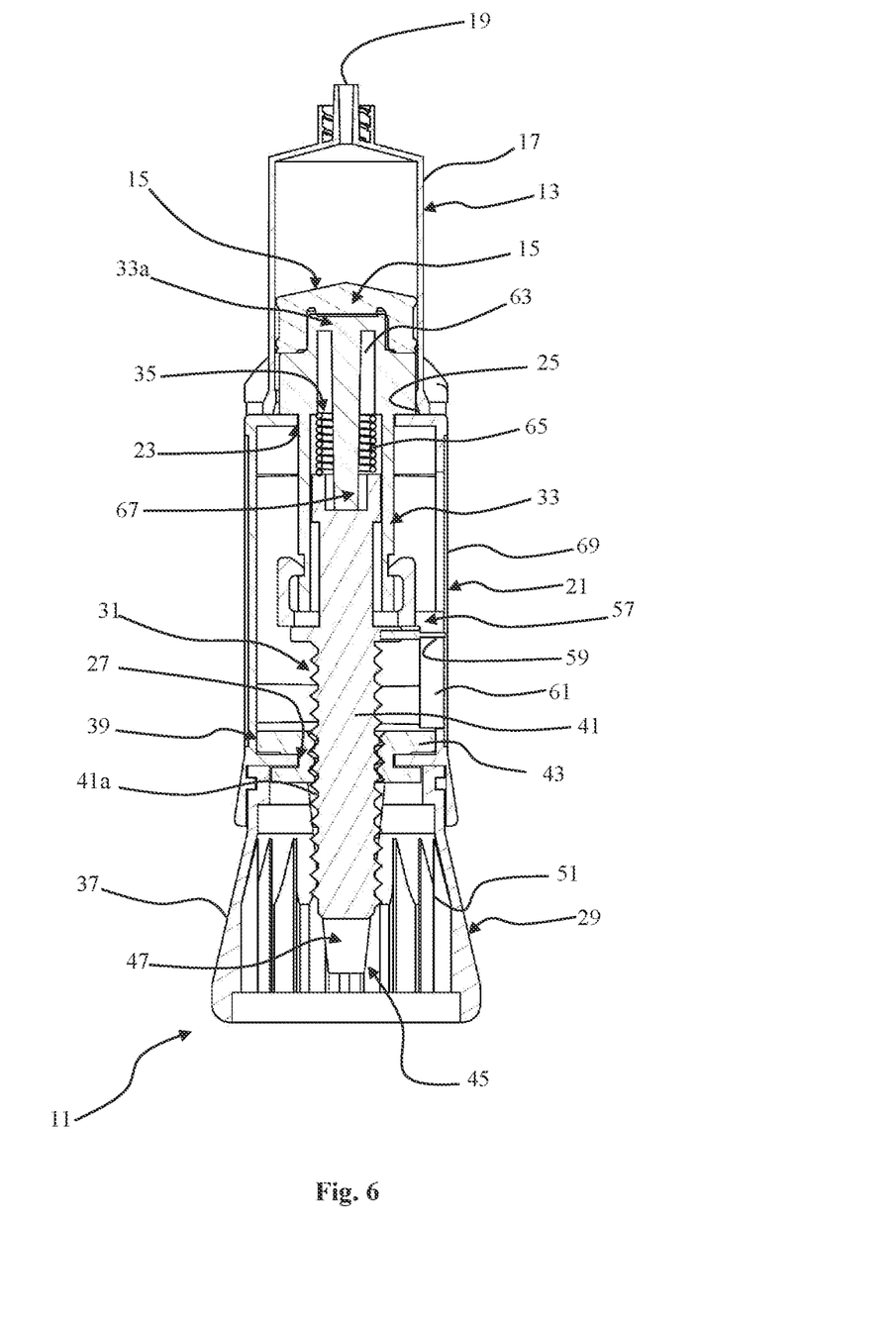
FIG. 6 is a sectional view along the second longitudinal plane of the pump of FIG. 1 when the syringe is full and the spring is loaded.

In a first step of the operation cycle of the pump 11, also referred to as priming step of the pump, where required, the knob 37 is rotated in the counter-clockwise direction to cause retraction of the first thrust member 31. Retraction of the first thrust member 31 occurs by virtue of the fact that the knob 37 is in engagement with the internally threaded nut 43, thanks to the cooperation between the arms 47 and the grooves 49 and projections 51. Rotation of the nut 43 causes the longitudinal retraction movement of the first thrust member 31 thanks to the provision of the threaded portion 41a along the rod 41. Retraction of the first thrust member 31 causes the two thrust members 31, 33 to move away from each other and, consequently, the spring 65 to relax. When the first thrust member 31 is completely retracted with respect to the second thrust member 33 (e.g., FIG. 4), the mutual interference between the two thrust members 31, 33 determined by corresponding abutment surfaces or mutual engagement, causes a corresponding simultaneous retraction of both thrust members 31, 33 during rotation of the knob 37 in the counter-clockwise direction. At the end of this step, the index 59 integral with the first thrust member 31 is positioned at a minimum value on the graduated scale 61 integral with the second thrust member 33.

In a second step of the working cycle of the pump 11, a syringe 13, filled with the drug, is attached to the pump body 21 at the opening 23 by engagement between the radial tabs 75 and the radial grooves 73. In this configuration, the plunger 15 of the syringe 13 is in a retracted position, i.e., proximal to the rear end 25 of the syringe 13, and the second thrust member 33 with its head 33a is frontally in abutment against the plunger 15.

In a third step of the operation cycle of the pump 11, also referred to as loading and infusion step, the knob 37 is rotated in the clockwise direction in order to cause advancement of the first thrust member 31. Advancement of the first thrust member 31 occurs by virtue of the fact that the knob 37 is in engagement with the internally threaded nut 43 thanks to the cooperation between the arms 47 and the grooves 49 and projections 51. Rotation of the nut 43 causes longitudinal movement of the first thrust member 31 thanks to the provision of the threaded portion 41a along the rod 41. As known, delivery of the drug through the front opening 19 of the syringe occurs with some difficulty, which also depends on the resistance to infusion, exerted by the patient's body and opposing longitudinal advancement of the plunger 15. Because of this, the longitudinal advancement of the first thrust member 31, caused by rotation of the knob 37, initially causes compression of the spring 65 within the seat 63 provided between the two thrust members 31, 33. When the effort required to cause further advancement of the first thrust member 31 is excessive and higher than a predetermined threshold, the friction mechanism 45 prevents further advancement of the first thrust member 31 by means of the actuation of the knob 37. At the end of this step, the index 59 integral with the first thrust member 31 is positioned at a maximum value on the graduated scale 61 integral with the second thrust member 33.

During this loading and infusion step, the elastic force of the spring 65, which is loaded because of the mutual approaching of the two thrust members 31, 33, causes gradual longitudinal movement of the second thrust member 33, advancement of the plunger 15, and consequent drug delivery through the front opening 19 of the syringe 13.

As the spring 65 releases its elastic energy stored during the loading step, the effort required to cause advancement of the first thrust member 31 becomes lower than the predetermined threshold and therefore the friction mechanism 45 allows to re-establish the engagement between the knob 37 and the nut 43. Thus, by acting again onto the knob 37, it is possible to restore again the load of the spring 65 until the predetermined threshold determining friction of the mechanism 45 is reached. According to the invention, this step of loading and relaxing the spring 65 can preferably occur several times in order to attain complete emptying of the syringe.

The invention as described is susceptible to several changes and modifications falling within the same inventive principle.

We claim:

1. A manually operated mechanical pump (11) for drug infusion through a syringe (13) comprising a syringe body (17) rearwardly attached to the pump (11) in a removable manner and provided with a plunger (15) longitudinally slidable within said syringe body (17) to cause a drug contained within said syringe body (17) to exit through a front opening (19) of the syringe (13), the pump (11) comprising a pump body (21) having a first, open front end (23), at which the syringe (13) is attached, and a second, open rear end (27), at which a drive member (29) is associated movably relative to the pump body (21), characterized in that a pair of longitudinally mutually movable thrust members (31,33) are provided between the drive member (29) and the syringe (13), said thrust members being adapted to impart a longitudinal thrust in the distal direction onto the plunger (15) of the syringe to cause the drug to exit through the front opening (19) of the syringe (13), and in that an elastic element (35) is provided between said thrust members, the elastic element being adapted to store elastic energy when a first one (31) of said thrust members (31,33) proximal to the drive member (29) is manually actuated by a user of the pump (11), and to release the stored elastic energy, thus causing a second one (33) of said thrust members (31,33) proximal to the syringe (13) to advance as the drug present within the syringe (13) is injected and exits through the front opening (19) of the syringe (13).

2. The mechanical pump (11) according to claim 1, wherein the drive member (29) comprises a knob (37) rotatably associated with the pump body (21) at the second, open rear end (27).

3. The mechanical pump (11) according to claim 2, wherein the first one (31) of the thrust members (31,33) is moveable longitudinally and is guided in its longitudinal movement by a rotatable guide (39) cooperating with the knob (37).

4. The mechanical pump (11) according to claim 3, wherein a longitudinal seat (63) housing the elastic element (35) is defined between the two thrust members (31, 33).

5. The mechanical pump (11) according to claim 4, wherein the longitudinal seat (63) provided between the two thrust members further houses a tip (67) which longitudinally interferes with the first one (31) or the second one (33) of the thrust members (31,33) when the thrust members (31,33) are in a configuration of minimum longitudinal distance between each other, a longitudinal extension of said tip (67) thus determines the minimum longitudinal distance between the two thrust members (31, 33) and a maximum longitudinal load of the spring (65).

6. The mechanical pump (11) according to claim 3, wherein the first one (31) of the thrust members (31,33) comprises a rod (41) having an externally threaded portion (41a), and wherein the rotatable guide (39) is internally threaded, whereby rotation of the rotatable guide (39) causes longitudinal movement of the rod (41).

7. The mechanical pump (11) according to claim 1, wherein a friction mechanism (45) is provided between the knob (37) and the rotatable guide (39), the friction mechanism being adapted to keep the knob (37) and the rotatable guide (39) in mutual engagement, when a force applied to the rotatable guide (39) and opposing rotation of the rotatable guide (39) is below a predetermined threshold.

8. The mechanical pump (11) according to claim 7, wherein an indicator (57) showing a load state of the elastic element (35) is provided between the two thrust members, the indicator being provided with an index (59) and a graduated scale (61) that are moveable relative to each other, the graduated scale (61) indicating at least one of a minimum value and a maximum value, that are visible from an outside of the pump body (21).

9. The mechanical pump (11) according to claim 1, wherein the elastic element (35) comprises a coil spring (65) adapted to be loaded longitudinally when a longitudinal mutual distance between the two thrust members (31, 33) decreases, and to discharge the stored elastic energy to move the two thrust members (31, 33) away from each other, thereby causing longitudinal sliding of the plunger (15) of the syringe (13) attached to the pump (11).

10. The mechanical pump (11) according to claim 9, wherein a longitudinal length of the spring (65) is chosen such that a difference between the longitudinal length of the spring (65) when the spring is in a maximum load configuration and the longitudinal length of the spring when the spring is in a fully relaxed configuration is lower than a longitudinal distance to be traveled by the plunger (15) of the syringe (13) in order to cause delivery of all the drug contained within the syringe (13), whereby it is necessary to perform more than one cycle of compression and relaxation of the spring (65) in order to empty the syringe (13).

11. The mechanical pump (11) according to claim 9, wherein a longitudinal seat (63) provided between the two thrust members further houses a tip (67) which longitudinally interferes with the first one (31) or the second one (33) of the thrust members (31,33) when the thrust members (31,33) are in a configuration of minimum longitudinal distance between each other, a longitudinal extension of said tip (67) thus determines the minimum longitudinal distance between the two thrust members (31, 33) and a maximum longitudinal load of the spring (65).

* * * * *